United States Patent
Boutet et al.

(10) Patent No.: US 9,579,081 B2
(45) Date of Patent: Feb. 28, 2017

(54) BIMODAL DIAGNOSTIC PROBE USING OPTICAL AND ULTRASONIC IMAGING, INCLUDING AT LEAST ONE REMOVABLE SHELL HAVING ON-BOARD OPTICAL MEANS

(75) Inventors: Jérôme Boutet, Claix (FR); An Nguyen-Dinh, La Riche (FR); Mathieu Debourdeau, Cusy (FR); Odile Messineo, Blois (FR); Christophe Notard, La Croix en Touraine (FR)

(73) Assignees: Commissariat à l'énergie atomique et aux énergies alternatives, Paris (FR); SA VERMON, Tours (FR)

( * ) Notice: Subject to any disclaimer, the term of this patent is extended or adjusted under 35 U.S.C. 154(b) by 263 days.

(21) Appl. No.: 14/123,352

(22) PCT Filed: Jun. 7, 2012

(86) PCT No.: PCT/EP2012/060815
§ 371 (c)(1),
(2), (4) Date: Feb. 26, 2014

(87) PCT Pub. No.: WO2012/168376
PCT Pub. Date: Dec. 13, 2012

(65) Prior Publication Data
US 2014/0187958 A1    Jul. 3, 2014

(30) Foreign Application Priority Data

Jun. 7, 2011    (FR) ...................................... 11 54960

(51) Int. Cl.
*A61B 8/14* (2006.01)
*A61B 8/00* (2006.01)
(Continued)

(52) U.S. Cl.
CPC ........ *A61B 8/4416* (2013.01); *A61B 1/00165* (2013.01); *A61B 1/042* (2013.01);
(Continued)

(58) Field of Classification Search
CPC ..... A61B 8/4416; A61B 8/445; A61B 8/4444; A61B 5/0084; A61B 1/303; A61B 5/0035;
(Continued)

(56) References Cited

U.S. PATENT DOCUMENTS

2004/0102821 A1* 5/2004 Kawata ................ A61B 5/0261
607/89
2006/0058614 A1* 3/2006 Tsujita ..................... A61B 8/12
600/407

(Continued)

FOREIGN PATENT DOCUMENTS

WO    2007 147262    12/2007

OTHER PUBLICATIONS

Boutet, J. et al., "De la lumire infrarouge pour guider les biopsies de la prostate", IRBM, Elsevier Masson, vol. 32, No. 2, pp. 123-125, XP028159431, (Jan. 23, 2011) (with English abstract).
(Continued)

*Primary Examiner* — Sanjay Cattungal
(74) *Attorney, Agent, or Firm* — Oblon, McClelland, Maier & Neustadt, L.L.P.

(57) ABSTRACT

A device for a bimodal diagnostic probe with optical and ultrasonic imaging, the probe including a main body supporting an ultrasonic transducer at its front end. The device includes a shell, an illumination mechanism mounted on a front end of the shell to light outside of the shell, and a collection or detection mechanism mounted on the front end of the shell to collect or detect an optical signal produced outside the shell. The shell includes an attachment mecha-
(Continued)

nism to reversibly assemble it around the main body of the probe, with the illumination mechanism and the collection or detection mechanism mounted on the shell.

16 Claims, 5 Drawing Sheets

(51) Int. Cl.
*A61B 8/12* (2006.01)
*A61B 1/00* (2006.01)
*A61B 1/04* (2006.01)
*A61B 1/07* (2006.01)
*A61B 1/31* (2006.01)
*A61B 1/303* (2006.01)
*A61B 5/00* (2006.01)

(52) U.S. Cl.
CPC ............... *A61B 1/07* (2013.01); *A61B 1/303* (2013.01); *A61B 1/31* (2013.01); *A61B 5/0035* (2013.01); *A61B 5/0084* (2013.01); *A61B 8/12* (2013.01); *A61B 8/445* (2013.01); *A61B 8/4411* (2013.01); *A61B 8/4444* (2013.01); *A61B 8/4483* (2013.01); *Y10T 29/49826* (2015.01)

(58) Field of Classification Search
CPC ......... A61B 8/4483; A61B 1/07; A61B 1/042; A61B 1/31; A61B 1/00165; A61B 8/4411; A61B 8/12; Y10T 29/49826
USPC ................................................. 600/437–480
See application file for complete search history.

(56) References Cited

U.S. PATENT DOCUMENTS

| | | | |
|---|---|---|---|
| 2008/0161696 A1* | 7/2008 | Schmitt | A61B 5/0066 600/467 |
| 2010/0040993 A1 | 2/2010 | Karazivan et al. | |
| 2011/0085721 A1 | 4/2011 | Guyon et al. | |
| 2011/0098572 A1* | 4/2011 | Chen | A61B 5/0062 600/463 |
| 2012/0157837 A1* | 6/2012 | Nagata | G01N 29/0672 600/437 |

OTHER PUBLICATIONS

International Search Report Issued Jul. 24, 2012 in PCT/EP12/060815 Filed Jun. 7, 2012.

* cited by examiner

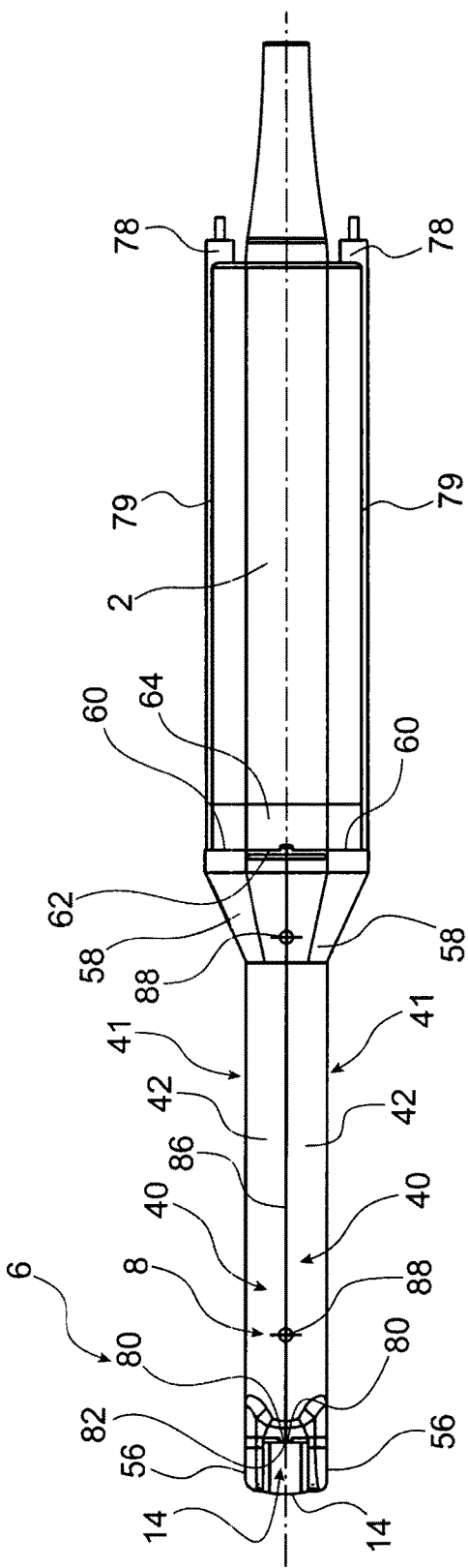
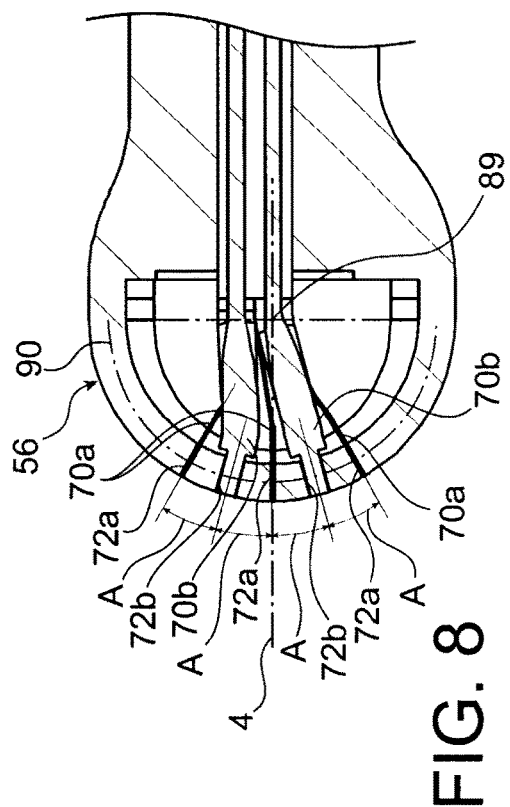
FIG. 7
FIG. 8

BIMODAL DIAGNOSTIC PROBE USING OPTICAL AND ULTRASONIC IMAGING, INCLUDING AT LEAST ONE REMOVABLE SHELL HAVING ON-BOARD OPTICAL MEANS

TECHNICAL FIELD

This invention relates to the field of bimodal diagnostic probes using optical and ultrasonic imaging.

It especially concerns endorectal bimodal probes intended for the diagnostic of prostate cancer. The invention may also be used for vaginal probes, or for any other diagnosis that may require optical imaging and ultrasonic imaging.

STATE OF PRIOR ART

Bimodal probes with optical and ultrasonic imaging have been developed recently, particularly in the field of detection of prostate cancer. One example embodiment is described in document '*Bimodal Ultrasound and Fluorescence Approach for Prostate Cancer Diagnosis*', Journal of Biomedical Optics 14(6), 2009).

This type of probe is particularly efficient due to the complementary of the two modes, optical imaging being capable of providing functional information with good contrast, while ultrasonic imaging provides morphological information with good resolution.

Thus, in early diagnosis of some pathologies, the approach consists of using optical and ultrasonic measurements to make a first positioning of potential tumours, and then to guide a biopsy tool that will take a sample of tissue in the suspected zone(s). An analysis of these tissues under a microscope can subsequently confirm whether or not they have a tumorous nature.

Although such probes are fully satisfactory for the functions that they provide, their design needs to be optimised. In particular, access to optical equipment may be complicated and require action by a specialised technician to make repairs and/or replace equipment. This also increases the complexity of manufacturing such probes.

PRESENTATION OF THE INVENTION

Therefore, the purpose of the invention is to at least partially remedy the disadvantages mentioned above that arise with embodiments according to prior art.

To achieve this, the first purpose of the invention is a bimodal diagnostic probe with optical and ultrasonic imaging comprising a main body with at least one ultrasonic transducer at its front end, said probe also comprising at least one device comprising a shell extending along a longitudinal direction between a back end and a front end that will at least partly form the front end of said probe, said device also comprising means of illumination mounted on said front end of the shell so as to provide illumination outside the shell, and collection or detection means mounted on said front end of the shell so as to collect or detect an optical signal produced outside said shell, According to the invention, the shell comprises attachment means so that it can be reversibly assembled around the main body of the probe, with illumination means and collection or detection means mounted on this shell.

Therefore, the invention is remarkable in that it provides a removable shell with on-board optical means, that simplifies the design of the bimodal probe on which the device will be assembled.

Repair and/or replacement operations of optical equipment on-board the shell may be initiated simply by removing this shell from the probe, which provides direct access to optical equipment without needing to take action on the acoustic means that remain in position on the probe. Consequently these operations may be done easily and quickly without the need for action by a specialised technician.

The simplified design of this invention also facilitates manufacturing of the bimodal probe, for which the acoustic means and optical means may be perfectly dissociated. For example, the optical means may easily be installed on their associated shell, for example by insertion and/or gluing.

Furthermore, as a result of this design, probe cleaning, disinfection and sterilisation phases are easily applied by removing the shell(s) with on-board optical means.

Finally, the reversible attachment means may be based on any design known to those skilled in the art. For example, possible assembly means include insertion, trapping, click fitting, screwing, etc.

Said illumination means are preferably associated with a first wiring, said collection or detection means are associated with a second wiring, and said first and second wirings pass longitudinally along said shell from said front end of the shell, at least as far as its back end. Preferably, these wirings are also mounted along the entire length of the shell. Consequently, they also accompany the shell as it is assembled on the probe around the main body and also during disassembly.

These wirings may be optical or electric, depending on the design adopted for illumination means and the collection or detection means installed on the front end of the shell.

In this respect, note that the illuminations means are designed to generate light. For example, a laser diode or a LED or a similar element could be used. When one element of this type is used to form all or some of the illumination means, it will be mounted directly at the front end of the shell. Its associated wiring will then be electrical wiring to connect this element to a source of electrical energy.

Alternately, all or some of the illumination means may be made with the aid of the end of an optical fibre called the optical excitation fibre that then forms said associated wiring. In such a case, this optical excitation fibre runs along the shell and then joins a remote light source that may be pulsed or continuous.

The detection means are designed to detect light, in other words to detect an optical signal. For example it may be a photodiode, a matrix optical sensor or any other similar element. When an element of this type is selected to form all or some of the detection means, it will be mounted directly at the front end of the shell. Its associated wiring will then be electrical wiring so as to connect this element to a source of electrical energy.

Alternately, collection means capable of capturing light may be routed towards remote detection means, for example of the type mentioned above. It may then be the end of an optical fibre, the fibre then forming said associated wiring, for routing the optical signal towards remote detection means. However, the optical fibre may then be replaced by any other light guide deemed to be appropriate by those skilled in the art, without going outside the framework of the invention.

Preferably, as mentioned above, said first wiring comprises at least a first optical fibre of which the front end mounted on the front end of the shell forms said illumination means, and said second wiring comprises at least one second optical fibre of which the front end mounted on the front end of the shell forms said collection means.

Even more preferably, said first wiring comprises a plurality of first optical fibres, the front end of each of which forms the illumination means, said second wiring comprises a plurality of second optical fibres, the front end of each of which forms the collection means, the front ends of the first and second optical fibres lying along at least one and preferably only one curved line lying in a plane.

Furthermore, for optimum performance, the front ends of the first and second optical fibres are preferably arranged alternating along a curved line which is preferably an arc of a circle.

Furthermore, the angular difference between the front end of any first fibre and each of the front ends of the two second directly consecutive fibres is between 5° and 25°, preferably between 10 and 20° and even more preferably of the order of 15°. These values, are very different from those usually used in prior art, that can considerably improve collection of the optical signal. Consequently, probe performances are considerably improved.

Preferably, said illumination means and said collection or detection means are flush with the outer surface of the shell. The absence of any protuberance prevents lesions on tissues with which the probe will come into contact. Alternately, these means could be set back from the outer surface of the shell, and the remaining orifice will then be filled with a transparent, translucid or diffusing material so that the front end of the shell has the smallest possible number of sharp edges.

Preferably, the probe comprises at least two devices with the shells jointly forming a casing all around the main body of the probe. Said shells also define a space at their front ends filled in by said at least one ultrasonic transducer. As indicated below, there are preferably two devices, but there may be more. In all cases, the shells of the devices are arranged to be adjacent along the circumferential direction of the probe.

Therefore, the probe preferably comprises two devices, with the two shells being arranged symmetrically about a plane passing through a longitudinal axis of the probe.

This design with two or several shells facilitates the installation of optical means on these shells, for example by providing reception means of the optical means directly on the inner surface of these shells, for example one or several grooves open on this inner surface. Obviously, this solution with several shells, including the solution with two complementary "half-shells", also facilitates repair and/or replacement operations of optical equipment on-board the shell.

Preferably, in the preferred case of two devices, each half-shell is globally concave, the concave face being oriented towards the longitudinal axis of the probe.

With the designs disclosed above, the shells define almost the entire part of the probe that will be inserted into the human body while the diagnostic is being done, except for the part covering the acoustic means. Alternately, these shells could also cover said at least one ultrasonic transducer provided that it is transparent to ultrasounds, without going outside the framework of the invention.

According to another envisaged embodiment, the bimodal probe is only equipped with one single-piece shell, which therefore extends around 360°. Consequently, cleaning and sterilisation operations are simplified. Furthermore, with the single-piece shell, the probe is more rigid.

Preferably, for the solution with several shells, the bimodal probe also comprises a material that fills these interfaces between the shells. This facilitates sterilisation of the probe without necessarily disassembling its shells with on-board optical means. Naturally, this biocompatible filling material of the silicon/elastomer type is selected so that it introduces minimum constraints on subsequent disassembly of the probe shells.

Preferably, the bimodal probe also comprises a gripping handle, the main body of which extends forwards, said handle being provided with one or several grooves on its outer surface, inside which the first and second wirings originating from the back end of the shell of each device fit.

Finally, note that the probe is preferably an endorectal probe that will be used for diagnosis of prostate cancer. Alternately, it may be a vaginal probe.

Another purpose of the invention is a method of fabricating a bimodal probe like that described above including the following steps:

equip the shell of each device with its illumination means and collection or detection means; then reversibly assemble each device around the main body of the probe.

In this description, the term fabrication should be understood in the broad sense of the term because it applies not only to fabrication of such a bimodal probe, but also to its repair that involves the two steps mentioned below, and also transformation of probe into a bimodal probe, always making use of the two steps mentioned below. In the latter case of transformation of an ultrasonic imaging probe into a bimodal probe according to the invention, a first step may consist of removing the original shell from the probe with ultrasonic imaging.

Finally, the purpose of the invention is a device for a bimodal diagnostic probe with optical and ultrasonic imaging, this probe being designed to comprise a main body comprising at least one ultrasonic transducer at its front end. The device comprises a shell extending along a longitudinal direction between a back end and a front end that will form at least part of the front end of the probe, this device also comprising illumination means mounted on the front end of the shell so as to provide illumination outside the shell, and collection or detection means mounted on the front end of the shell so as to collect or detect an optical signal produced outside the shell.

According to the invention, the shell comprises attachment means for reversibly assembling it around the main body of the probe, with illumination and collection or detection means mounted on this shell.

Furthermore, said illumination means are associated with a first wiring, said collection or detection means are associated with a second wiring, and said first and second wirings are routed longitudinally along said shell from said front end of the shell at least as far as its back end.

Furthermore, said first wiring comprises a plurality of first optical fibres, the front ends of each of which forms illumination means, said second wiring comprises a plurality of second optical fibres, the front end of each of which forms collection means, and the front ends of the first and second optical fibres lie on at least one curved line that is the arc of a circle.

Furthermore, the angular difference between the front end of any first fibre and each of the front ends of the two directly consecutive second fibres is between 5° and 25°, preferably between 10 and 20°, and even more preferably of the order of 15°. These values are very different from values usually used in prior art, and considerably improve collection of the optical signal. Consequently, the performances of the associated probe are significantly improved.

Other advantages and characteristics of the invention will become clear in the detailed non-limitative description given below.

BRIEF DESCRIPTION OF THE DRAWINGS

This description will be made with reference to the appended drawings among which;

FIG. 7 represents a top view of the probe shown in the previous figures;

FIG. 8 represents a diagrammatic side view showing the arrangement of optical means on the front end of the shell shown in FIGS. 4 and 5;

DETAILED DESCRIPTION OF PREFERRED EMBODIMENTS

Figure 1:
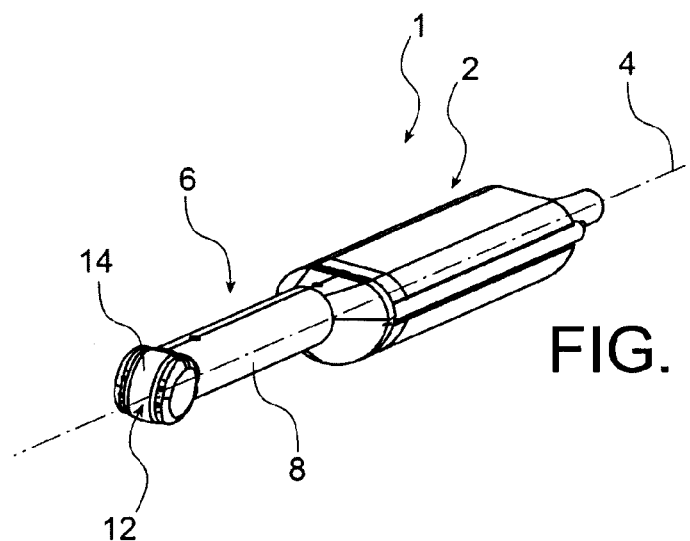
FIG. 1 represents a perspective view of a bimodal diagnostic probe according to a preferred embodiment of this invention.
Figure 2:
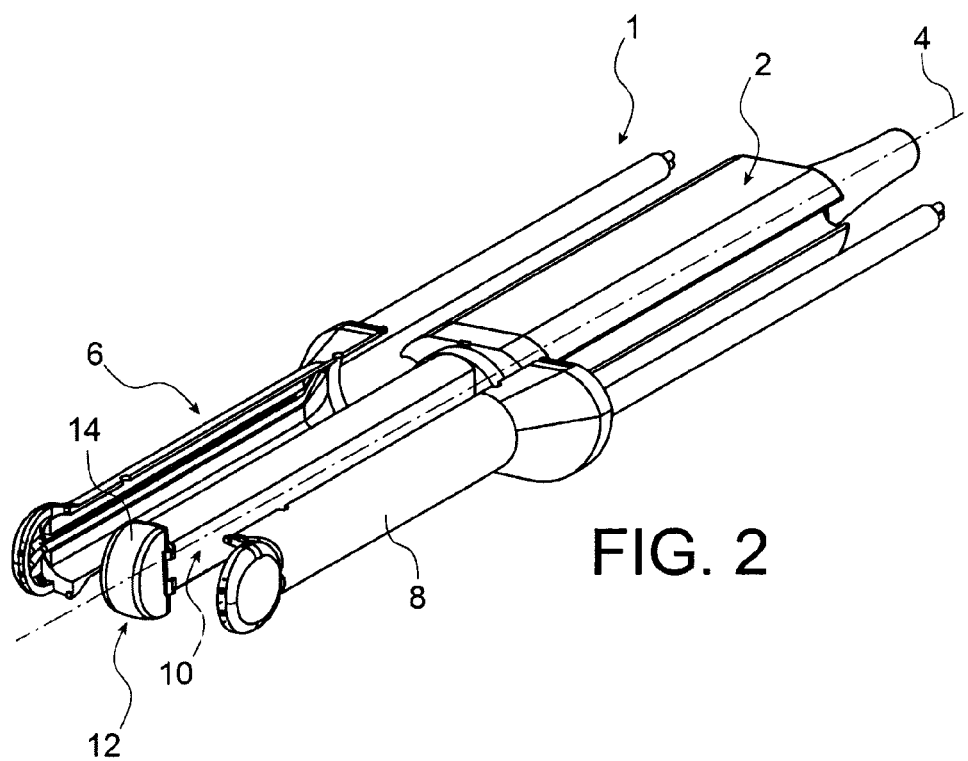
FIG. 2 is an exploded view of the probe shown in FIG. 1.
Figure 3:
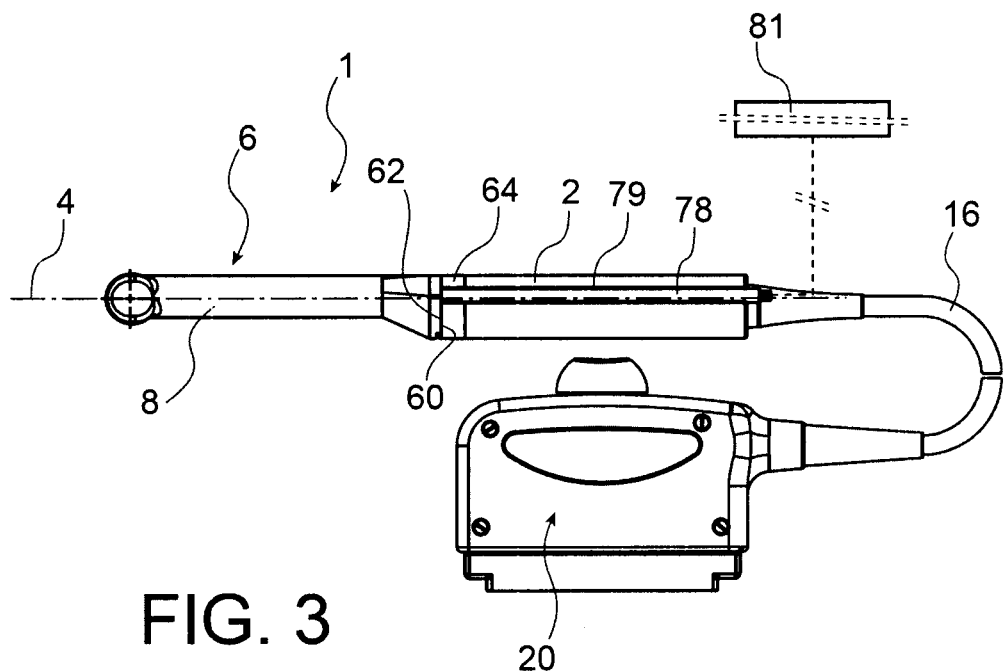
FIG. 3 represents a side view of the probe shown in the previous figures, coupled with an imaging system.
Figure 4:
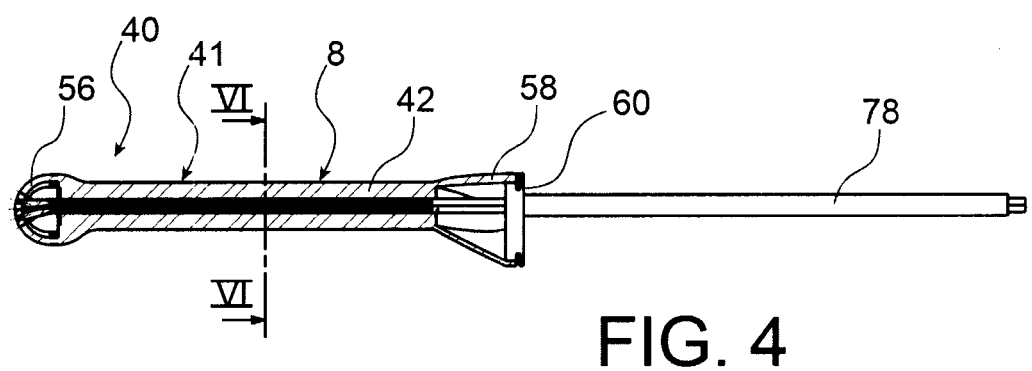
FIG. 4 represents a longitudinal section of one of two removable shell devices equipped with optical means, provided on the probe shown in the previous figures.

Firstly with reference to FIGS. 1 to 3, the figures show an endorectal probe 1 according to a preferred embodiment of this invention.

This diagnostic probe is bimodal in the sense that it uses optical imaging and ultrasonic imaging. It comprises an elongated gripping handle 2 with an axis 4 defining the longitudinal direction of the probe. The handle 2 is prolonged forwards along the direction of the axis 4, by an insertion part 6 that will be inserted into the anatomic region to be investigated.

The insertion part 6 thus has a smooth outer surface 8, essentially formed by two removable shells with on-board optical means that will be described in detail below. On the inside, this insertion part 6 is formed by an elongated main body 10, approximately cylindrical with axis 4. At its back end, the main body 10 is supported by the handle 2, while its front end comprises acoustic means 12 in the form of one or several ultrasonic transducers covered at the front by a protection 14 made of a type material forming part of said smooth outer surface 8. This protection 14 is naturally transparent to ultrasounds, is biocompatible and seals the probe.

The ultrasonic transducer(s) may be linear or in the matrix form and have a plane, convex or concave surface geometry. In the preferred embodiment represented, the transducer is a linear network with a convex surface geometry, providing a sectorial angle of vision. In this case, the transducer 14 is globally in the form of a half-disk, the plane face of which is orthogonal to the axis 4 towards the back of the probe.

Electric wiring 16 is connected to the transducer 12 and is routed through the main body 6 and then through the handle 2 to exit at a back end of the handle. The electric wiring 16 is then connected to an ultrasonic imaging system 20 shown in FIG. 3.

Note that one or several electronic multiplexing modules may be placed between the transducers 12 and the imaging system 20, to reduce the number of wiring connection cables 16. These modules may be installed either in the main body 10 or in the handle 2, without going outside the framework of the invention.

As mentioned above, the probe is fitted with two devices each in the form of a removable shell on which the optical means are mounted. These devices 40 will now be described in detail with reference to FIGS. 4 to 7.

They are arranged symmetrically around the main body 4 along a longitudinal plane passing through the axis 4. Each of these two devices 40 has a shell 41, the central part 42 of which passes along the main body of the probe 10. This central part 42 is cylindrical, with an axis parallel to the axis 4. The straight section of this part 42 is globally C-shaped, the inside of the C being oriented towards the main body of the probe 10, and the outside part of it forms a part of the smooth outside surface 8. More precisely, the inside of the C has a flat 44 that will come into plane contact with a corresponding plane surface 46 of the main body of the probe 10, as can be seen better in FIGS. 5 and 6. Furthermore, the inner faces 50 of the two ends of the C cooperate with complementary cylindrical surfaces 52 with a circular section provided on the main body of the probe 10, between the two plane surfaces 46. These cooperations of shapes ensure that the shells 41 are correctly oriented relative to the main body of the probe 10.

At the front, the shell 41 includes a front end element 56 globally in the shape of a disk, curved slightly outwards and that will come into contact with one of the two side edges of the transducer 12. The axis of this disk is orthogonal to the axis 4. When the two shells 41 are assembled on the probe, the two front end elements 56 and the transducer 12 together define a front end of the probe with a generally spherical, possibly truncated shape, or a cylindrical shape with its axis orthogonal to the axis 4.

At the back, the shell 41 includes a back end element 58 that is tapered as far as a plane back end surface 60 orthogonal to the axis 4. This surface 60 will come into plane contact with a complementary surface 62 provided on a widened base 64 of the main body 10 of the probe, mounted at the front end of the handle 2.

Elements 42, 56, 58 of the shell 41 are preferably made of a single piece, preferably from a polyurethane type plastic material that is also biocompatible and that seals the probe.

One of the special features of this invention lies in the fact that each shell 41 is provided with on-board optical means, in this case formed from optical fibres passing along the shell, along the axis 4. It includes firstly a first wiring comprising a plurality of first optical fibres 70a, the front ends 72a of each of which form illumination means that will provide illumination outside the probe, being installed on the front periphery of the element 56.

It also includes a second wiring comprising a plurality of second optical fibres 70b, the front ends 72b of each of which form collection means that will collect an optical signal produced outside the probe, through the first optical fibres 70a mentioned above. These front ends 72b are also mounted on the front periphery of the element 56.

For information, the fibres 70a called the optical excitation fibres, have a sheathed diameter of the order of 155 μm, while the fibres 70b called the detection fibres have a sheathed diameter of the order of 2.1 mm. In the preferred embodiment shown, each shell 41 is equipped with three first optical fibres 70a, and two second optical fibres 70b.

Figure 5:
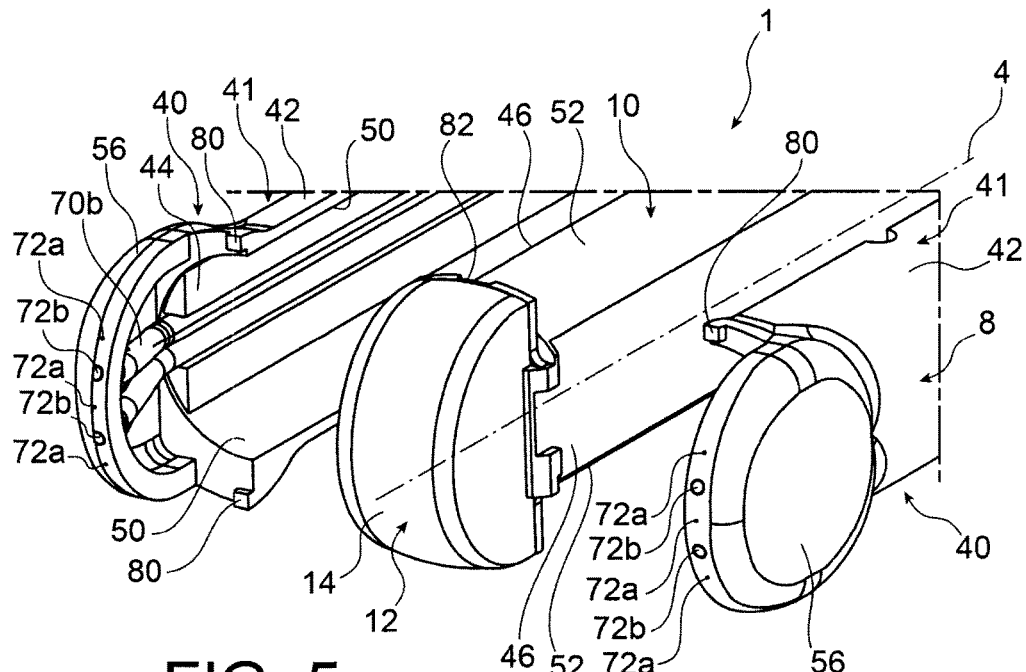
FIG. 5 represents an exploded perspective view of a front part of the probe shown in the previous figures.

All front ends 70b, 72b of the optical fibres are flush with the outer surface 8 of the shell 41 to prevent lesions on tissues in contact with which the probe will be applied. To achieve this, these front ends 70b, 72b pass through the thickness of the element 56 to open up from the probe towards the front, as can be seen in FIG. 5.

Figure 6:
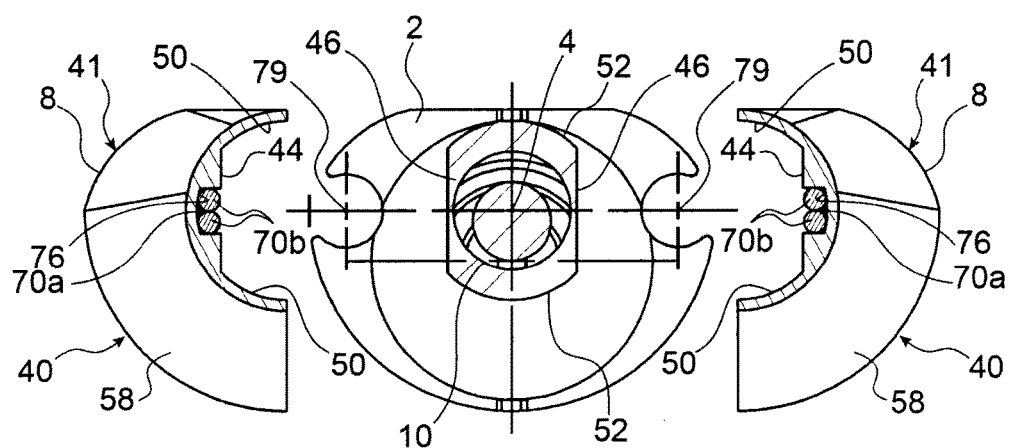
FIG. 6 represents a sectional view along line VI-VI in FIG. 4.

Therefore the fibres 70a, 70b extend from the front end of the shell 41 where they form the illumination means 72a and collection means 72b, and then pass backwards along the inner surface of the shell in a groove 76 formed on the flat 44, as can be seen in FIG. 6. This groove 76 correctly guides the optical fibres 70a, 70b and facilitates their installation and replacement if necessary.

These fibres extend beyond the back end of the shell 41, starting from where they are housed in a sheath 78. This sheath is inserted in a longitudinal groove 79 formed on the outer surface of the handle 2, and are then connected to an optical imaging system 81 shown diagrammatically in FIG. 3, incorporating a pulsed or continuous light source. This junction may be made by quick fasteners.

Each shell 41 has the special feature that it can be assembled reversibly around the main body of the probe 10, with its on-board optical equipment. To achieve this, it is fitted with appropriate attachment means, in this case comprising pins 80 supported by the front end element 56. More precisely, the element 56 has two diametrically opposite pins 80, each of which will be inserted in a notch 82 provided on the outside casing of the transducer 12. Each of the two notches 82 is designed to hold two pins 80 side by side, each belonging to one of the two shells 41. The contact obtained between the two pins housed in one notch combined with the contacts of each of these two pins with the side edges of the notch, hold the pins in this notch. Furthermore, the plane contact at the back end of the shells between the complementary surfaces 60, 62, blocks the shells relative to the main body of the probe.

Therefore, the reversible assembly of the shells 41 around the main body of the probe 10 can be treated as a clip fitting, since the pins are inserted in their corresponding notches.

When they are assembled on the probe, the shells 41 form a casing surrounding the main body of the probe 10. This casing is made by the two central parts 42 and by the two back end elements 58.

On the other hand, these shells 41 define a space between the two front end elements 56 occupied by the transducer 12 as can be seen in FIG. 7 in particular. Junction interfaces between the two shells reference 86 can also be seen in this figure. The grooves created at these interfaces are filled in with a filling material, to obtain the smoothest possible outer surface 8. This facilitates sterilisation of the probe without necessarily disassembling its shells with on-board optical means. Naturally, this silicon/elastomer type of biocompatible filling material is selected so that it introduces minimum constraints on subsequent disassembly of probe shells, for example achieved by applying a separation force using pins inserted into special purpose orifices 88 formed at the interfaces 86 as can be seen in FIG. 7. This filling material is also applied at the interfaces between the shells and the ultrasonic transducer.

With reference to FIG. 8, it can be seen that the front ends 72a, 72b of the optical fibres 70a, 70b on each shell are arranged to alternate along an arc of a circle 90 with centre 89, this arc of circle 90 with a diameter similar to the front end element 56 through which the front ends 72a, 72b of the fibres pass, are in a plane parallel to the axis 4. When the shells are assembled, the two arcs of a circle 90 are arranged parallel to each other on each side of the transducer and the longitudinal axis 4.

Furthermore, the angular difference A between the front end 72a of each first fibre 70a and each of the front ends 72b of two directly consecutive second fibres 70b is preferably of the order of 15°. This value of about 15° can considerably improve collection of the optical signal. Consequently, performances of the probe are significantly improved.

Figure 9:
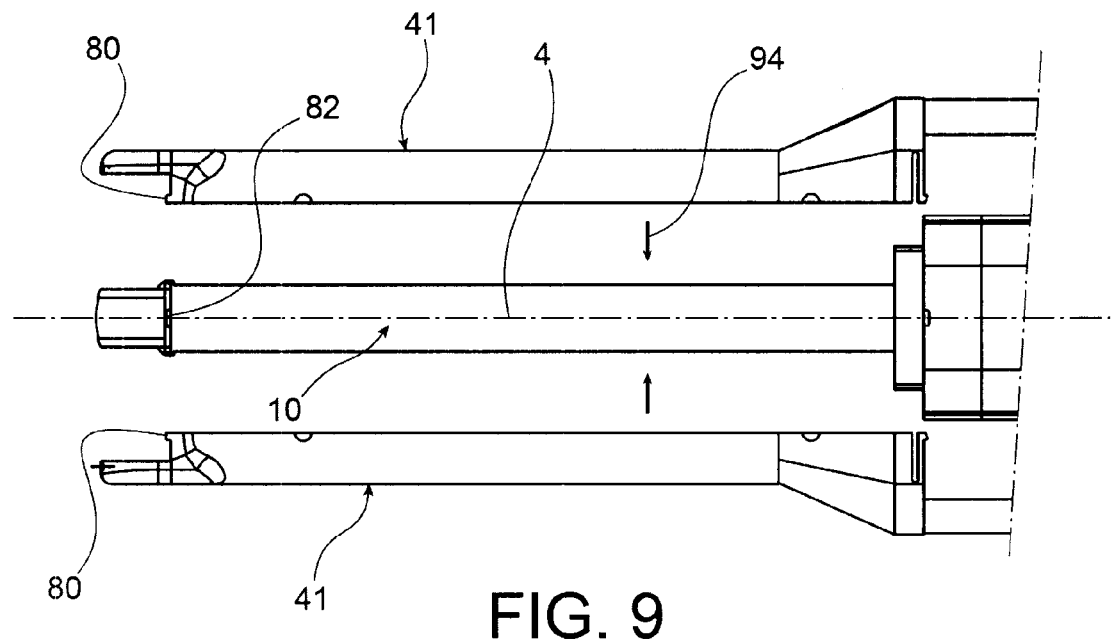
FIG. 9 diagrammatically represents a view showing the assembly of two removable devices with a shell fitted with optical means, on the probe.

The invention also relates to a method of fabricating the bimodal probe that has just been described. This method consists firstly of fitting each shell 41 with its optical fibres 70a, 70b, inserting them laterally in their groove 76 on the inner surface of the shell. These shells with on-board optical means are then assembled reversibly around the main body of the probe as shown diagrammatically in FIG. 9. This assembly is made by bringing the two shells towards each other along a direction 94 orthogonal to the axis 4, around the main body 10, until the pins 80 are clipped into position in the corresponding notches 82.

Figure 10:
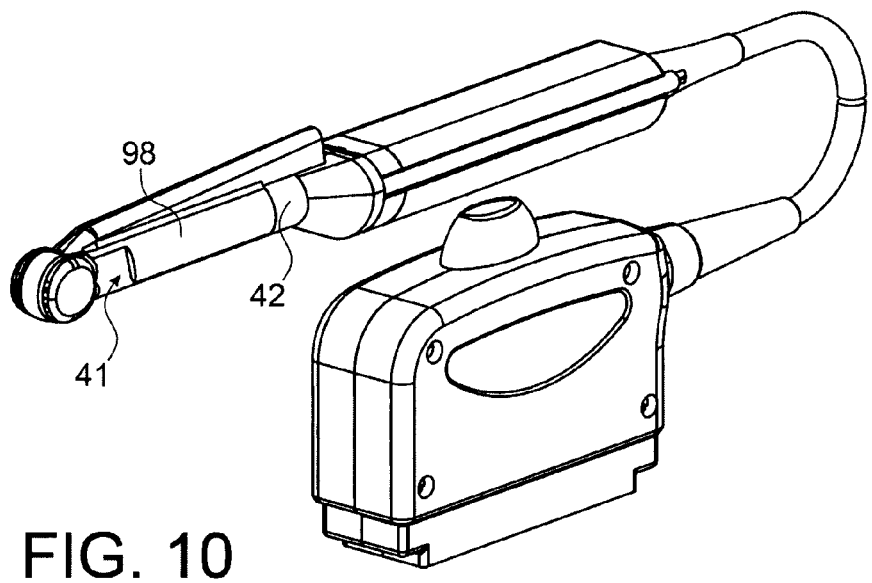
FIG. 10 diagrammatically represents a perspective view of the probe shown in the previous figures, on which a biopsy tool designed to take a tissue sample is mounted.

Once the reversible assembly has been made, a biopsy tool 98 can be installed on the outside on the shells 41 to take a tissue sample in the suspect zone(s), also by clip fitting about the central parts 42 as shown in FIG. 10.

Obviously, those skilled in the art can make various changes to the invention disclosed above simply as a non-limitative example.

The invention claimed is:

1. A bimodal diagnostic probe with optical and ultrasonic imaging comprising:
    an elongated main body having a back end and a front end, and including at least one ultrasonic transducer at the front end of the main body;
    at least one device comprising:
        a shell extending along a longitudinal direction between the back end and the front end of the main body, the shell having a front that will at least partly form a front end of the probe,
        means of illumination mounted on the front end of the shell to provide illumination outside the shell,
        collection or detection means mounted on the front end of the shell to collect or detect an optical signal produced outside the shell, and
        attachment means for removably attaching the shell radially outward of the main body and around the main body of the probe, wherein the illumination means and collection or detection means are mounted on the shell.

2. A probe according to claim 1, wherein the illumination means is associated with a first wiring, wherein the collection or detection means is associated with a second wiring, and the first and second wirings pass longitudinally along the shell from the front end of the shell, at least as far as the back end of the shell.

3. A probe according to claim 2, wherein the first wiring comprises at least one first optical fiber including a fiber front end, mounted on the front end of the shell, and which forms the illumination means.

4. A probe according to claim 2, wherein the second wiring comprises at least one second optical fiber including a fiber front end, mounted on the front end of the shell, and which forms the collection means.

5. A probe according to claim 2, wherein the first wiring comprises a plurality of first optical fibers including repective fiber front ends that form the illumination means, wherein the second wiring comprises a plurality of second optical fibers including respective fiber front ends that form the collection means, and wherein the fiber front ends of the first and second optical fibers lie along at least one curved line.

6. A probe according to claim 5, wherein the fiber front ends of the first and second optical fibers are arranged alternating along a curved line.

7. A probe according to claim 5, wherein the at least one curved line is an arc of a circle.

8. A probe according to claim 7, wherein an angular difference between the fiber front end of any first fiber and each of the fiber front ends of two second directly consecutive fibers is between 5° and 25°, or is between 10 and 20°, or is of an order of 15°.

9. A probe according to claim 1, wherein the illumination means and the collection or detection means are flush with an outer surface of the shell.

10. A probe according to claim 1, comprising at least two devices, with the respective shells of the devices forming a casing all around the main body of the probe, and the shells define a space at their respective front ends filled in by the at least one ultrasonic transducer.

11. A probe according to claim 10, wherein, the two shells being arranged symmetrically about a plane passing through a longitudinal axis of the probe.

12. A probe according to claim 10, further comprising a material that fills the interfaces between the shells.

13. A probe according to claim 1, comprising a single device, with one single-piece shell extending around 360° about the longitudinal axis of the probe.

14. A probe according to claim 2, further comprising a gripping handle from which the main body extends forwards, and wherein the gripping handle including one or plural grooves on its outer surface, into which fit the first and second wirings originating from a back end of the shell of each device.

15. A probe according to claim 3, as an endorectal or vaginal probe.

16. A method of fabricating a bimodal probe according to claim 1, comprising:

equipping the shell of each device with its illumination means and collection or detection means; then reversibly assembling each device around the main body of the probe.

* * * * *